(12) United States Patent
Nakayama et al.

(10) Patent No.: US 9,279,102 B2
(45) Date of Patent: Mar. 8, 2016

(54) TEMPERATURE-RESPONSIVE SUBSTRATE FOR CELL CULTURE AND PRODUCTION METHOD THEREOF

(75) Inventors: Masamichi Nakayama, Tokyo (JP); Teruo Okano, Tokyo (JP)

(73) Assignee: TOKYO WOMEN'S MEDICAL UNIVERSITY, Tokyo (JP)

( * ) Notice: Subject to any disclaimer, the term of this patent is extended or adjusted under 35 U.S.C. 154(b) by 476 days.

(21) Appl. No.: 13/819,685

(22) PCT Filed: Aug. 31, 2011

(86) PCT No.: PCT/JP2011/069839
§ 371 (c)(1),
(2), (4) Date: Feb. 27, 2013

(87) PCT Pub. No.: WO2012/029882
PCT Pub. Date: Mar. 8, 2012

(65) Prior Publication Data
US 2014/0212973 A1    Jul. 31, 2014

(30) Foreign Application Priority Data

Aug. 31, 2010  (JP) ................................ 2010-208506

(51) Int. Cl.
*B05D 1/00* (2006.01)
*C12N 5/00* (2006.01)
*C08F 293/00* (2006.01)

(52) U.S. Cl.
CPC .......... *C12N 5/0068* (2013.01); *C08F 293/005* (2013.01); *C08F 2438/03* (2013.01); *C12N 2539/10* (2013.01)

(58) Field of Classification Search
CPC ..... B05D 1/005; C12N 5/0068; C09D 153/00
USPC .......................................... 435/396; 427/240
See application file for complete search history.

(56) References Cited

FOREIGN PATENT DOCUMENTS

| JP | 1990-211865 A | 8/1990 |
| JP | 1993-192138 A | 8/1993 |
| JP | 09-169850 | 6/1997 |
| JP | 2008-220354 | 9/2008 |
| WO | 2010/010837 A1 | 1/2010 |
| WO | WO 2010010837 A1 * | 1/2010 ........... C12N 5/0068 |
| WO | 2010/027081 A1 | 3/2010 |

OTHER PUBLICATIONS

Loh et al. (Soft Matter 2009, 5, 2937-2946).*

(Continued)

*Primary Examiner* — Vu A Nguyen
(74) *Attorney, Agent, or Firm* — Kilpatrick Townsend & Stockton LLP (57) ABSTRACT

To form a temperature-responsive surface for cell culture by simple processes, said temperature-responsive surface for cell culture being capable of efficiently culturing cells. Cultured cells or a cell sheet can be efficiently removed from the temperature-responsive surface for cell culture by merely changing the temperature of the substrate surface. To coat the substrate surface with a block copolymer, in which a water insoluble polymer segment is coupled with a temperature-responsive polymer segment, in an amount of 0.8 to 3.0 μg/cm² of the temperature-responsive polymer.

11 Claims, 10 Drawing Sheets

(56) References Cited

OTHER PUBLICATIONS

Loh et al., "Novel poly(N-isopropylacrylamide)-poly[®-3-hydroxybutyratel]-poly(N-isopropylacrylamide) triblock copolymer surface as a culture substrate for human mesenchymal stem cells") Soft Matter, 2009, vol. 5, pp. 2937-2946.

Moran et al., "Intact endothelial cell sheet harvesting from thermoresponsive surfaces coated with cell adhesion promoters," J. R. Soc. Interface, 2007, vol. 4, pp. 1151-1157.

International Search Report, Oct. 11, 2011, PCT application No. PCT/JP2011/069839, 2 pages.

Extended European Search Report corresponding to EP 11821897.3 dated Feb. 24, 2015, 4 pages.

* cited by examiner

| SAMPLE NAME | $M_n{}^a$ | $M_w/M_n{}^b$ | NUMBER OF MONOMERS[c] | | RATE OF PIPAAm IN POLYMER (wt%) |
|---|---|---|---|---|---|
| | | | BMA | IPAAm | |
| B79-IP24 | 14300 | 1.06 | 79 | 24 | 19 |
| B79-IP60 | 18300 | 1.21 | 79 | 60 | 37 |
| B79-IP120 | 25100 | 1.24 | 79 | 120 | 54 |
| B79-IP223 | 36700 | 1.29 | 79 | 223 | 69 |
| B79-IP315 | 47200 | 1.21 | 79 | 315 | 76 |
| B36-IP52 | 11300 | 1.17 | 36 | 52 | 52 |
| B142-IP231 | 46600 | 1.42 | 142 | 231 | 56 |

[a,c] DETERMINED BY $^1$H-NMR, [b] DETERMINED BY GPC

Fig.3

| SAMPLE NAME | CONCENTRATION (w/v%) [a] | AMOUNT OF GRAFTED PIAAm [μg/cm$_2$] [b] | |
|---|---|---|---|
| | | BEFORE | AFTER [c] |
| B79-IP120 | 0.1 | 0.87 ± 0.03 | 0.94 ± 0.01 |
| | 0.3 | 1.44 ± 0.00 | 1.37 ± 0.03 |
| | 0.5 | 1.81 ± 0.06 | 1.73 ± 0.01 |
| PIPAAm | 0.5 | 2.50 ± 0.08 | 0.46 ± 0.05 |

[a] POLYMER CONCENTRATION FOR SPIN COATING
[b] DETERMINED BY ATR/FT-IR
[c] SOAKED IN WATER AT 37°C FOR 24 HOURS, IMMERSED IN WATER AT 4°C FOR 24 HOURS, AND THEN VACUUM-DRIED.

B79-IP120 (MOLECULAR WEIGHT:25100, RATE OF PIPAAm IN POLYMER:54 wt%)
PIPAAm (MOLECULAR WEIGHT:12000)

SOLVENT: ACETONITRILE/N, N-DIMETHYLFORMAMIDE (5/1, V/V)
SPIN COATING TREATMENT ON A POLYSTYRENE FOR CELL CULTURE (TCPS) (3000 rpm, 30 sec)

Fig.4

| SAMPLE NAME | POLYMER CONCENTRATION (w/v%) [a] | AMOUNT OF GRAFTED PIPAAm (μg/cm²) | CONTACT ANGLE (cos θ) [b] | |
|---|---|---|---|---|
| | | | 20 °C | 37 °C |
| B79-IP24 | 0.3 | 0.72 ± 0.06 | 0.79 ± 0.02 | 0.75 ± 0.02 |
| B79-IP60 | 0.3 | 1.18 ± 0.06 | 0.73 ± 0.02 | 0.73 ± 0.02 |
| B79-IP120 | 0.1 | 0.87 ± 0.04 | 0.74 ± 0.01 | 0.76 ± 0.01 |
| B79-IP120 | 0.3 | 1.44 ± 0.01 | 0.75 ± 0.01 | 0.78 ± 0.02 |
| B79-IP120 | 0.5 | 1.81 ± 0.08 | 0.78 ± 0.01 | 0.79 ± 0.01 |
| B79-IP223 | 0.3 | 1.60 ± 0.04 | 0.83 ± 0.00 | 0.80 ± 0.00 |
| B79-IP315 | 0.3 | 1.63 ± 0.05 | 0.84 ± 0.01 | 0.79 ± 0.01 |
| B36-IP52 | 0.3 | 1.32 ± 0.03 | 0.70 ± 0.01 | 0.67 ± 0.01 |
| B142-IP231 | 0.3 | 1.45 ± 0.01 | 0.77 ± 0.01 | 0.78 ± 0.00 |
| UpCell® | – | NO DATA | 0.85 ± 0.01 | 0.78 ± 0.01 |
| TCPS | – | – | 0.88 ± 0.01 | 0.87 ± 0.01 |

[a] POLYMER CONCENTRATION FOR SPIN COATING ON TCPS (3000 rpm, 30 sec)
[b] DETERMINED BY CONTACT ANGLE MEASUREMENT

Fig.5

BOVINE ARTERIAL ENDOTHELIAL CELLS (BAEC) WERE SEEDED AT $5.0 \times 10^3$ cells/cm$^2$

| SAMPLE NAME | CONCENTRATION (w/v%)ᵃ | RATE OF PIPAAm IN POLYMER (wt%) | AMOUNT OF GRAFTED PIPAAm ($\mu$g/cm²) | COLLECTION OF CELL SHEET AT 20°C | TIME UNTIL REACHING CONFLUENCE (BAEC SEEDING: $1.0 \times 10^5$ cells/cm²) |
|---|---|---|---|---|---|
| B79-IP120 | 0.05 | 54 | 0.54 | NOT DESORBED | 3 days |
| | 0.1 | 54 | 0.87 | 20-24 hr | 3 days |
| | 0.3 | 54 | 1.44 | 15-20 min | 3 days |
| | 0.5 | 54 | 1.81 | 15-20 min | >7 days |
| B79-IP24 | 0.3 | 19 | 0.72 | NOT DESORBED | 3 days |
| B79-IP60 | 0.3 | 37 | 1.18 | ABOUT 40 min | 3 days |
| B79-IP223 | 0.3 | 69 | 1.60 | 15-20 min | >7 days |
| B79-IP315 | 0.3 | 76 | 1.63 | 15-20 min | >7 days |
| B36-IP52 | 0.3 | 52 | 1.32 | ABOUT 20 min | 3 days |
| B142-IP231 | 0.3 | 56 | 1.45 | 15-20 min | >7 days |

TEMPERATURE-RESPONSIVE SUBSTRATE FOR CELL CULTURE AND PRODUCTION METHOD THEREOF

TECHNICAL FIELD

The present invention relates to cell culture substrates useful in, e.g., biological and medical fields. This application claims priority to Japanese Patent Application No. 2010-208506 filed on Aug. 31, 2010.

BACKGROUND ART

Recently, animal cell culture techniques have been remarkably developed, and also research and development related to animal cells have been carried out in a wide variety of fields. The animal cells have been used not only for commercializing them at the early stage of development or for commercializing products from the cells, but also for analyzing cells and their surface proteins to design useful medicines or for performing treatment by growing the cells of patients in vitro or enhancing the function of the cells, followed by returning the cells into the bodies of the patients. At present, many researchers pay attention to the techniques for culturing animal cells.

Many animal cells including human cells are anchorage-dependent cells. Therefore, in order to culture animal cells in vitro, the cells need to be once attached to a scaffold substrate. Under such a background, many researchers have previously designed and devised substrate surfaces that are more desirable for cells. However, all these techniques are involved in those during cell culture. Cultured anchorage-dependent cells produce adhesive proteins when they adhere to a substrate. Therefore, in conventional techniques, the adhesive proteins need to be destroyed, e.g., by enzymatic treatment or the like for detaching the cells. Consequently, these techniques have a drawback in that cell surface proteins, which are specific for each cell and are produced from the cells during culturing them, are also simultaneously destroyed. However, any countermeasures against this problem have not been found or investigated.

Under such a background, Japanese Laid-open Patent Publication No. 2-211865 (Patent Literature 1) describes a novel method of culturing cells, comprising the step of culturing cells on a cell culture support coated with a polymer whose upper or lower critical solution temperature in water is 0 to 80° C., at the upper critical solution temperature or less, or the lower critical solution temperature or more, and then detaching the cultured cells without enzymatic treatment by increasing the culturing temperature to the upper critical solution temperature or more, or decreasing the culturing temperature to the lower critical solution temperature or less. Japanese Laid-open Patent Publication No. 05-192138 (Patent Literature 2) describes that skin cells are detached with low damage from a cell culture substrate, by culturing skin cells on the temperature-responsive cell culture substrate described in Japanese Laid-open Patent Publication No. 2-211865 (Patent Literature 1), at the upper critical solution temperature or less, or the lower critical solution temperature or more, and then increasing the culturing temperature to the upper critical solution temperature or more, or decreasing the culturing temperature to the lower critical solution temperature or less. In addition, Japanese Patent Application No. 2007-105311 (Patent Literature 3) describes a method of repairing the surface protein of the cultured cells using the temperature-responsive cell culture substrate described in Japanese Laid-open Patent Publication No. 2-211865 (Patent Literature 1). Such use of the temperature-responsive cell culture substrate has allowed various developments of conventional culture techniques.

However, the conventional techniques have problems in that the surface of a chemically inert engineering plastic must be coated with a polymer by using high energy such as electron beams, a large-scale apparatus such as an electron beam irradiation apparatus is needed for coating the surface, and thus the cell culture substrate inevitably becomes expensive.

In order to solve such problems, some techniques have been previously developed. As described in, e.g., Soft Matter, 5, 2937-2946 (2009) (Non Patent Literature 1) or Interface, 4, 1151-1157 (2007) (Non Patent Literature 2), a method of coating a substrate surface with a polymer having a particular molecular structure is known. However, all the techniques do not reach the technical level in which cells can be cultured, similarly to a case where the conventional cell culture substrates are used, and the level in which the cells can be detached only by changing temperature, similarly to a case where the temperature-responsive cell culture substrate which is produced by using the above-described electron beams, or the level in which cultured cells can be detached as a cell sheet when they become confluent.

CITATION LIST

Patent Literature

Patent Literature 1: Japanese Laid-open Patent Publication No. 2-211865
Patent Literature 2: Japanese Laid-open Patent Publication No. 05-192138
Patent Literature 3: Japanese Patent Application No. 2007-105311

Non Patent Literature

Non Patent Literature 1: Soft Matter, 5, 2937-2946 (2009)
Non Patent Literature 2: Interface, 4, 1151-1157 (2007)

SUMMARY OF INVENTION

Technical Problem

The present invention is intended to solve the problems of the conventional techniques as described above. That is, the present invention is directed to a provision of a novel temperature-responsive substrate for cell culture, created based on an idea quite different from those of the conventional techniques, and a production method thereof.

Solution to Problem

The present inventors have investigated from various angles in order to solve the above-mentioned problems. As a result, it was surprisingly found that by use of a substrate whose base material surface is coated with a block copolymer, in which a water insoluble polymer segment is coupled with a temperature-responsive polymer segment, in an amount of 0.8 to 3.0 $\mu g/cm^2$ of the temperature-responsive polymer, cells can be efficiently cultured, and the cultured cells or a cell sheet can be efficiently detached only by changing the temperature of the substrate surface. The present inventors focused on the heterogeneity of the block copolymer in which the water insoluble polymer segment is coupled with the temperature-responsive polymer segment, and on the morphology of the block copolymers on the substrate surface.

Through the extensive research, the inventors have reached the above findings. In addition, it has been found that the performance of such a substrate for cell culture is higher than that of the conventional temperature-responsive substrates for cell culture. The present invention has been completed based on these findings.

In accordance with the present invention, there is provided a temperature-responsive substrate for cell culture, wherein the surface of the cell culture is coated with a block copolymer, in which a water insoluble polymer segment is coupled with a temperature-responsive polymer segment, in an amount of 0.8 to 3.0 µg/cm$^2$ of the temperature-responsive polymer. The temperature-responsive cell culture substrate according to the present invention includes, but is not limited to, preferred embodiments described below.

In accordance with one embodiment of the present invention, a base material surface of the substrate is coated with the block copolymer in an amount of 0.09 to 7.0 mg/cm$^2$ of the water insoluble polymer.

In accordance with one embodiment of the present invention, the substrate surface has a phase separation structure.

In accordance with one embodiment of the present invention, a content of the temperature-responsive polymer in the block copolymer is 30 to 90 wt %.

Figure 2:
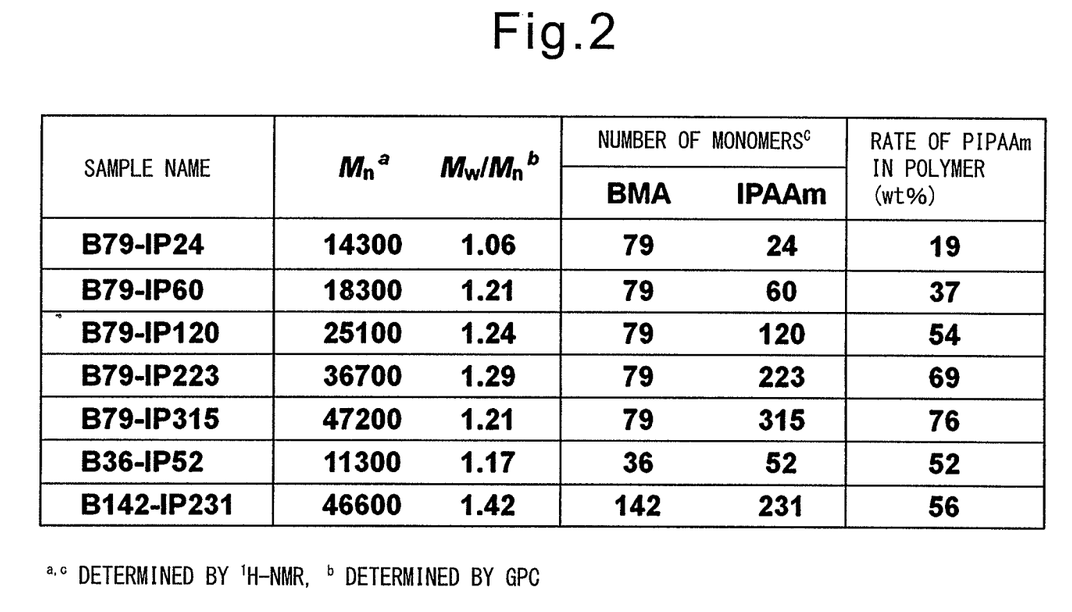
FIG. 2 shows the characteristics of the block copolymers obtained in Example 1.

In accordance with one embodiment of the present invention, an average molecular weight of the temperature-responsive polymer in the block copolymer is 3000 or more. Since the ratio of a weight average molecular weight (Mw) to a number average molecular weight (Mn) is almost 1 as indicated in FIG. 2, any average molecular weight may be adopted for the benefit from the present invention.

In accordance with one embodiment of the present invention, the temperature-responsive polymer includes any one or more of poly-N-substituted acrylamide derivatives, poly-N-substituted methacrylamide derivatives, their copolymers, and polyvinyl methyl ethers.

In accordance with one embodiment of the present invention, the temperature-responsive polymer is poly-N-isopropylacrylamide.

In accordance with one embodiment of the present invention, a base material of the substrate is one plate-shaped base material, or a combination of two or more plate-shaped base materials.

In accordance with the present invention, there is provided a method for producing a temperature-responsive substrate for cell culture, comprising the steps of: dissolving or dispersing in an organic solvent a block copolymer in which a water insoluble polymer segment is coupled with a temperature-responsive polymer segment; applying the block copolymer solution homogeneously to a base material surface by spin coating; and drying the surface. The method for producing a responsive substrate for cell culture according to the present invention includes, but is not limited to, preferred embodiments described below.

In accordance with one embodiment of the present invention, the block copolymer is obtained by reversible addition-fragmentation chain transfer (RAFT) polymerization.

In accordance with one embodiment of the present invention, the solvent in which the block copolymer is dissolved is a liquid mixture of acetonitrile and N,N-dimethylformamide.

In accordance with one embodiment of the present invention, a volume ratio of acetonitrile to N,N-dimethylformamide in the liquid mixture is 5:1.

Advantageous Effects of Invention

According to the temperature-responsive substrate for cell culture of the present invention, cells can be efficiently cultured, and the cultured cells or a cell sheet can be efficiently detached only by changing the temperature of a substrate surface. In addition, according to the present invention, such a functionalized surface can be easily prepared.

DESCRIPTION OF EMBODIMENTS

The present invention relates to a temperature-responsive substrate for cell culture, wherein a base material surface of the substrate is coated with a block copolymer, in which a water insoluble polymer segment is coupled with a temperature-responsive polymer segment, in an amount of 0.8 to 3.0 µg/cm$^2$. It has an advantage in that the water insoluble polymer moiety of, the block copolymer which coats on a base material surface of the substrate is not detached from the surface during not only the cell culture step, but also the detachment step of cultured cells or a cell sheet by changing temperature.

"Block copolymer" generally means a polymer having at least two compositionally different segments. As understood by those skilled in the art, examples of the block copolymer include diblock copolymers, triblock copolymers, random block copolymers, star-branched block copolymers and hyperbranched block copolymers. A block copolymer used in the present invention typically has a water insoluble polymer segment (A) and a temperature-responsive polymer segment (B). The block copolymer may also have any one of the following structures: A-B structure containing two block segments; A-B-A or B-A-B containing three block segments; and -(A-B)$_n$- (wherein n is an integer of 2 or more) containing a plurality of blocks. The block copolymer used in the temperature-responsive substrate for cell culture of the present invention preferably has the A-B structure in light of the above-mentioned structures. As used herein, when the block copolymer having the A-B structure includes, e.g., a poly-n-butyl methacrylate (PBMA) segment as a water insoluble polymer segment (A) and a poly-N-isopropylacrylamide (PI-PAAm) segment as a temperature-responsive polymer segment (B), the block copolymer may be denoted as "B79-IP120", using the number of monomer units in each polymer (e.g., 79 units of BMA and 120 units of IPAAm) (see Example 1).

"Water insoluble polymer" as used herein is not particularly limited as long as it is insoluble in water. Examples of the water insoluble polymer include polyalkyl acrylates such as poly-n-butyl acrylate and poly-t-butyl acrylate; polyalkyl methacrylates such as poly-n-butyl methacrylate, poly-t-butyl methacrylate, and polymethyl methacrylate; polystyrenes; and the like.

"Temperature-responsive polymer" as used herein means a polymer having a lower critical solution temperature (LCST) and/or a polymer having an upper critical solution temperature (UCST). It may also be any of homopolymers, copolymers and mixtures thereof. For example, it includes polymers described in Japanese Patent Publication No. 06-104061. Specifically, such polymers are obtained by, e.g., homopolymerization or copolymerization of monomers described below. Examples of the monomers to be used include (meth)acrylamide compounds, N- (or N,N-di)alkyl substituted (meth)acrylamide derivatives, vinyl ether derivatives, and partially acetified products of polyvinyl alcohol. For the copolymers, any two or more of these monomers may be used. In addition, copolymers with monomers other than the above-mentioned monomers, graft- or co-polymers of polymers, or mixtures of polymers and/or copolymers, may also be used. Further, the polymers may be optionally cross-linked as long as the inherent properties of the polymers are not impaired.

Since a substance to be separated is usually a biological substance, it is preferable to select a temperature-responsive polymer suitable for separating a biological substance of interest in the range of 5° C. to 50° C. The temperature-responsive polymer which can be used in the present invention may also be any one or a combination of two or more of poly-N-substituted acrylamide derivatives, poly-N-substituted methacrylamide derivatives, their copolymers, and polyvinyl methyl ethers. More specifically, examples of the temperature-responsive polymer include poly-N-n-propylacrylamide (lower critical solution temperature (LCST) of homopolymer: 21° C.), poly-N-n-propylmethacrylamide (LCST of homopolymer: 27° C.), poly-N-isopropylacrylamide (LCST of homopolymer: 32° C.), poly-N-isopropylmethacrylamide (LCST of homopolymer: 43° C.), poly-N-cyclopropylacrylamide (LCST of homopolymer: 45° C.), poly-N-ethoxyethylacrylamide (LCST of homopolymer: about 35° C.), poly-N-ethoxyethylmethacrylamide (LCST of homopolymer: about 45° C.), poly-N-tetrahydrofurfurylacrylamide (LCST of homopolymer: about 28° C.), poly-N-tetrahydrofurfurylmethacrylamide (LCST of homopolymer: about 35° C.), poly-N,N-ethylmethylacrylamide (LCST of homopolymer: 56° C.), poly-N,N-diethylacrylamide (LCST of homopolymer: 32° C.), and the like. Poly-N-isopropylacrylamide is preferred.

According to the present invention, the content of the temperature-responsive polymer in the above-mentioned block copolymer may range from 30 to 90 wt %, may preferably range from 40 to 85 wt %, and may further preferably range from 45 to 60 wt %. In the case of less than 30 wt %, it is difficult for cultured cells on the polymer to detach by changing temperature, and thus operation efficiency is considerably deteriorated. Therefore, such a case is unfavorable. In contrast, in the case of more than 90 wt %, it is difficult for cells to adhere to the polymer region. Since it becomes difficult to adhere cells to the polymers, such a case is unfavorable for the cell culture substrate of the present invention. Such a case is also unfavorable since the amount of a water insoluble polymer moiety in the block copolymer is low and thus the block polymer may be easily detached from the substrate surface.

The temperature-responsive polymer as used in the present invention may have an average molecular weight of 3000 or more, preferably 5000 or more, further preferably 10000 or more, most preferably 12000 or more. In the case of the molecular weight of less than 3000, it is difficult for cultured cells on the polymer to detach by changing temperature, and thus operation efficiency is considerably deteriorated. Therefore, such a case is unfavorable. In addition, in accordance with the present invention, when the molecular weight of the temperature-responsive polymer has the above-mentioned lower limit, cultured cells can be efficiently detached without limitation by the upper limit of the molecular weight. In one embodiment, the upper limit of the average molecular weight of the temperature-responsive polymer may also be 35000 and is preferably 30000, more preferably 25000.

The temperature-responsive substrate for cell culture of the present invention is coated with the above-mentioned block copolymer in an amount of 0.8 to 3.0 μg/cm$^2$, preferably 0.9 to 2.0 μg/cm$^2$, further preferably 1.3 to 1.8 μg/cm$^2$, of the temperature-responsive polymer. In the case of the coating amount of less than 0.8 μg/cm$^2$, it is difficult for cultured cells on the block copolymer to detach by changing temperature, and thus operation efficiency is considerably deteriorated. Therefore, such a case is unfavorable. In contrast, in the case of more than 3.0 μg/cm$^2$, it is difficult for cells to adhere to the polymer region. Since it becomes difficult to adhere cells to the polymers, such a case is unfavorable for the cell culture substrate of the present invention. The coating amount may be measured according to a common procedure, and any method may be used. For example, a FT-IR-ATR method, an elemental analysis method, ESCA, and the like may be used.

The temperature-responsive substrate for cell culture according to the present invention is characterized in that a base material surface of the substrate is coated with a block copolymer in which a water insoluble polymer segment is coupled with a temperature-responsive polymer segment in a predetermined ratio. When the content of the temperature-responsive polymer in the block copolymer is more than 90 wt % (that is, when the content of the water insoluble polymer in the block copolymer is less than 10 wt %), the block copolymer is prone to be detached from the base material surface of the substrate, as described above. Therefore, 10 wt % or more of the "water insoluble polymer" in the block copolymer is preferred. In addition, when the cell sheet is produced according to the present invention, the amount of the coated temperature-responsive polymer, which is a main constituent of the block copolymer, is important. Therefore, the content of the water insoluble polymer in the block copolymer may be appropriately adjusted so that the base material surface of the culture substrate can be coated with the temperature-responsive polymer in the above-mentioned desired amount range. More specifically, the base material surface of the temperature-responsive substrate for cell culture according to the present invention may also be coated with the above-mentioned block copolymer in an amount of 0.09 to 7.0 μg/cm², preferably 0.14 to 4.5 μg/cm², further preferably 0.2 to 3.0 μg/cm² of the water insoluble polymer.

As described above, the block copolymer of the present invention includes the water insoluble polymer segment coupled with the temperature-responsive polymer segment which has an affinity for water. Therefore, it is expected that when a the base material surface of the substrate is coated with this block copolymer and dried, a phase separation structure such as a fine lamella structure, a sea-island structure, a cylinder structure, or a co-continuous structure is formed on the surface. The morphology, size, and the like of the phase separation structure are not particularly limited. When cells adhere to the substrate surface, existence of the phase separation structure on the substrate surface is preferred, since degeneration of the cells can be inhibited.

Generally, a reversible addition-fragmentation chain transfer (RAFT) polymerization method, an atom transfer radical polymerization (ATRP) method, an anionic polymerization method, or a living radical polymerization method is commonly used for producing a block copolymer. In the present invention, although a method for producing a block copolymer is not limited to the above-mentioned and the other polymerization methods, it is preferable to use the RAFT polymerization method. When a block copolymer is produced using the RAFT polymerization method, a dithioester-based functional group which is a moiety of a RAFT agent remains in a terminal of the obtained block copolymer. This is specific to the RAFT polymerization method, and further polymerization reaction can be initiated from the terminal after the RAFT polymerization reaction. In this case, the dithioester-based functional group present in the terminal of the temperature-responsive polymer is easily converted to a thiol group by adding 2-ethanolamine or the like. This reaction can be easily performed in a short time without special conditions. As a result, a polymer chain with a highly reactive thiol group can be obtained. By use of the thiol group, a functionalized molecule with a functional group such as a maleimide group and a thiol group, etc., can be selectively and efficiently introduced into the terminal of the polymer chain. Thus, new functionality can be imparted on the surface of the temperature-responsive substrate for cell culture according to the present invention. Examples of the functional group include, but are not limited to, a hydroxyl group, a carboxyl group, an amino group, a carbonyl group, an aldehyde group, a sulfonate group, and the like. In addition, a peptide or protein which can accelerate cell adhesion may also be immobilized on the polymer chain terminal described above. In this context, it is also expected that introduction of the functional group into the polymer chain terminal will provide a new procedure for controlling the temperature responsiveness of the substrate surface from a different standpoint, since the lower critical solution temperature (LCST) of a polymer such as poly-N-isopropylacrylamide varies depending on the hydrophilicity and hydrophobicity of a terminal functional group.

As described above, the block copolymer of the present invention is obtained by the RAFT polymerization method, that is, a method of performing radical polymerization in the presence of a RAFT agent to grow a temperature-responsive polymer. Examples of initiators used in this method include, but are not particularly limited to, 2,2'-azobis(isobutyronitrile), 2,2'-azobis(4-methoxy-2,4-dimethylvaleronitrile) (V-70), 2,2'-azobis[(2-carboxyethyl)-2-(methylpropioneamidine)](V-057), and the like. In accordance with the present invention, a polymer chain can be grown by these initiators. In addition, examples of the RAFT agent for the present invention include, but are not particularly limited to, benzyl dithiobenzoate, cumyl dithiobenzoate, 2-cyanopropyldithiobenzoate, 1-phenylethylphenyldithioacetate, cumyl phenyldithioacetate, benzyl 1-pyrrolecarbodithioate, cumyl 1-pyrrolecarbodithioate, and the like.

A solvent used for polymerization in the present invention is not particularly limited, but benzene, 1,4-dioxane, dimethylformaldehyde (DMF), or the like is preferred. The solvent can be appropriately selected, without limitation, depending on the kinds of a monomer, a RAFT agent, and a polymerization initiator which are used in a polymerization reaction.

The present invention is a method of growing a polymer having hydration force varying within the temperature range of 0 to 80° C. from monomers by a surface-initiated radical polymerization method in which an initiator is used in the presence of a RAFT agent in a solvent such as 1,4-dioxane. Initiator concentration, RAFT agent concentration, reaction temperature, reaction time, and the like during polymerization are not particularly limited, but may be changed depending on a purpose. In addition, a reaction liquid may be left standing or stirred. Since RAFT polymerization according to the present invention can proceed without any metal ions, the reaction product can be easily purified. In addition, the reaction procedure is simple. Therefore, RAFT method is preferred.

The temperature-responsive substrate for cell culture according to the present invention is typically obtained by dissolving or dispersing in a solvent the block copolymer obtained as described above, and then homogeneously coating a base material surface with the copolymer. In this case, the solvent is not particularly limited, but it may be appropriately selected from the solvents which can dissolve or disperse the block copolymer without almost dissolving the base material surface. Examples of the solvent include N,N-dimethylacrylamide, isopropyl alcohol, acetone, tetrahydrofuran, 1,4-dioxane, dimethylsulfoxide, methyl ethyl ketone, N,N-dimethylacetamide, chloroform, dichloromethane, or acetonitrile, N,N-dimethylformamide, and the like. When a plurality of solvents are used, a mixing ratio of the solvents is not particularly limited, but in the case of a liquid mixture of acetonitrile and N,N-dimethylformamide, for example, it is preferable that a volume ratio of acetonitrile to N,N-dimethylformamide is 5:1, 4:1, or 6:1. There is a method of using water as a solvent, and optionally adding an emulsifier for dissolving, emulsifying and dispersing a block copolymer. However, in the case using such method, the block copolymer may not be present homogeneously in water, depending on the composition thereof. As a result, the base material surface is not homogeneously and smoothly coated with the block copolymer, cells do not adhere homogeneously to the substrate surface during the process of cell culture, and thus the cells cannot be proliferated homogeneously. Therefore, such a method is not preferable for coating the base material. In addition, when the base material surface is coated with the block copolymer, use of water as a solvent is not preferred, since it takes a lot of time to dry the substrate surface after the application of the block copolymer.

In accordance with the present invention, it is necessary to apply the above-mentioned block copolymer solution homogeneously to a base material surface. Examples of a method for applying the solution include, but are not particularly limited to, a method of utilizing a spin coater, a method of leaving a base material standing on a horizontal table, and the like. The temperature-responsive substrate for cell culture according to the present invention is obtained by removing the solvent after the application of the block copolymer solution. Examples of methods for removing the solvent include, but are not particularly limited to, a method of slowly evaporating a solvent at room temperature in the atmosphere, a method of slowly evaporating a solvent at room temperature in a solvent-saturated condition, a method of evaporating a solvent by heating, a method of evaporating a solvent by reducing pressure, and the like. The former two methods are preferable for producing the temperature-responsive substrate for cell culture having a clean surface, and the method of slowly evaporating a solvent at room temperature in a solvent-saturated condition is more preferable.

As the base material of the cell culture substrate which is coated with the block copolymer, not only glass, modified glass, polystyrene, polymethyl methacrylate, polyethylene terephthalate, polycarbonate, and the like, which are usually used for cell culture, but also materials which can be formed in arbitrary shapes including, but not limited to, polymer compounds other than the above, ceramics, metals, and the like, can be used. The shape of the base material of the cell culture substrate is not limited to cell culture dishes such as Petri dishes, but a plate (plate-shaped base material), fiber (filamentous base material), (porous) particle (granular base material), tube-shaped base material, or film-shaped base material, or a combination of two or more thereof is also acceptable. A base material in the shape of a container commonly used for cell culture (flask, etc.) is also acceptable. Preferably, the base material of the cell culture substrate for the present invention is one plate-shaped base material, or a combination of two or more plate-shaped base materials. In addition, when the above-mentioned base material of the cell culture substrate is coated with a block copolymer, the surface of the base material is preferably hydrophobic. Thus, when a base material with a hydrophilic surface, such as a glass plate, is used, it is preferable to be subjected to hydrophobization treatment beforehand. The hydrophobization treatment may be, without particular limitation, a treatment using a silane coupling agent (e.g., hexyltriethoxysilane).

Cells which can be cultured on the surface of the temperature-responsive substrate obtained by the present invention are not limited by their origin. In addition, a source and a preparing method of the cells are not particularly limited. Examples of the cells used in the present invention include animal cells, insect cells, plant cells, bacteria, and the like. Typically, animal cells are preferably originated from human, monkey, dog, cat, rabbit, rat, nude mouse, mouse, guinea pig, pig, sheep, Chinese hamster, bovine, marmoset, African green monkey, and the like. In addition, a medium used in the present invention is not particularly limited as long as it is a medium for animal cells. The medium is, for example, serum-free media, serum-containing media, or the like. A differentiation-inducing substance such as retinoic acid or ascorbic acid may also be further added to such a medium. The seeding density of cells on the substrate surface can be appropriately changed, and the seeding density can be determined according to a common procedure.

In addition, when the temperature-responsive substrate for cell culture according to the present invention is used, cultured cells or a cell sheet can be detached without enzymatic treatment only by changing temperature of the culture substrate to the upper critical solution temperature or more, or to the lower critical solution temperature or less of the polymer coated on the base material of the culture substrate. The above-mentioned detachment can be performed in culture fluid or in another isocratic liquid, and can be performed depending on a purpose. For the purpose of detaching and collecting cells more quickly and more efficiently, a method of tapping or shaking the substrate, a method of stirring a medium using a pipette, or the like may also be used singly or in combination.

Cells obtained from each tissue can be efficiently cultured by using the temperature-responsive substrate for cell culture according to the present invention. Use of this culturing method makes it possible to detach cultured cells or a cell sheet efficiently without damage only by changing temperature. Previously, such an operation needs efforts and skills of an operator. However, the present invention does not need them, and thus large amounts of cells can be handled. The culture substrate surface of the present invention can be produced by a living radical polymerization method. Particularly, the culture substrate surface can be easily and precisely designed, and a functional group can be easily introduced into a molecular chain terminal by a RAFT polymerization method (one of living radical polymerization methods). Therefore, the temperature-responsive substrate for cell culture according to the present invention and the producing method thereof are remarkably advantageous cell culture techniques.

EXAMPLES

The present invention will be further explained with reference to the following examples, but it is not limited thereto at all.

Example 1

Preparation and Characteristics of Temperature-Responsive Surfaces

In the present example, temperature-responsive block copolymers including a segment of poly-N-isopropylacrylamide (PIPAAm) which is a temperature-responsive polymer and a segment of poly-n-butyl methacrylate (PBMA) which is a water insoluble polymer were prepared, and spin-coated on the surfaces of the base materials. For the surfaces coated with the temperature-responsive block copolymers, physical properties such as the amounts of the polymers introduced on the surfaces and surface wettability were evaluated. Temperature-dependent change of cell adhesiveness to the substrate surfaces was also investigated.

(1) Preparation of Temperature-Responsive Block Copolymer

Figure 1:
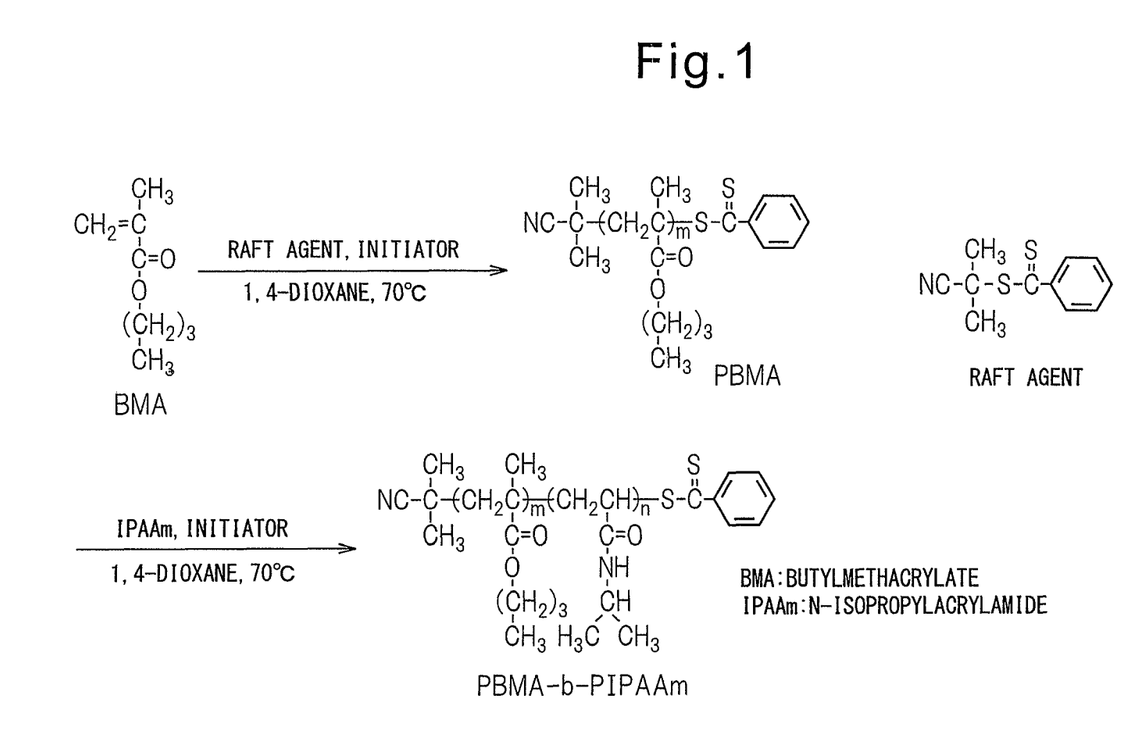
FIG. 1 shows a synthetic route of block copolymers in Example 1.

Specifically, PBMA-b-PIPAAm block copolymers were prepared using PBMA, which is a water insoluble polymer synthesized by RAFT polymerization, as a macro RAFT agent (FIG. 1). In addition, the analysis values for PBMA and PBMA-b-PIPAAm synthesized with controlling molecular weights by RAFT polymerization are listed in FIG. 2. In the present specification, for example, the PBMA-b-PIPAAm block copolymer in which a monomer-unit ratio of BMA to IPAAm is 70:24 is denoted as "B79-IP24".

(2) Characteristics of Temperature-Responsive Block Copolymers

The obtained polymers were evaluated by nuclear magnetic resonance spectrometry ($^1$H-NMR) and gel permeation chromatography (GPC). PBMA-b-PIPAAm was dissolved at each concentration of 0.1 w/v %, 0.3 w/v %, or 0.5 w/v % in a liquid mixture of acetonitrile/N,N-dimethylformamide (5/1 in v/v). In addition, a PBMA solution (0.5 w/v %) and PIPPAm (0.5 w/v %) were similarly prepared as controls. Then, a surface of a polystyrene (TCPS), which is a base material of a cell culture substrate, was spin-coated with the polymer solution (3000 rpm, 30 sec), and dried overnight at room temperature, and the substrate surface was then washed with water and dried under reduced pressure at room temperature for 6 hours to prepare a temperature-responsive surface. Also, TCPS which was not coated with the polymer solution, and UpCell (registered trademark) (manufactured by CellSeed Inc., Japan) were used as controls.

Figure 3:
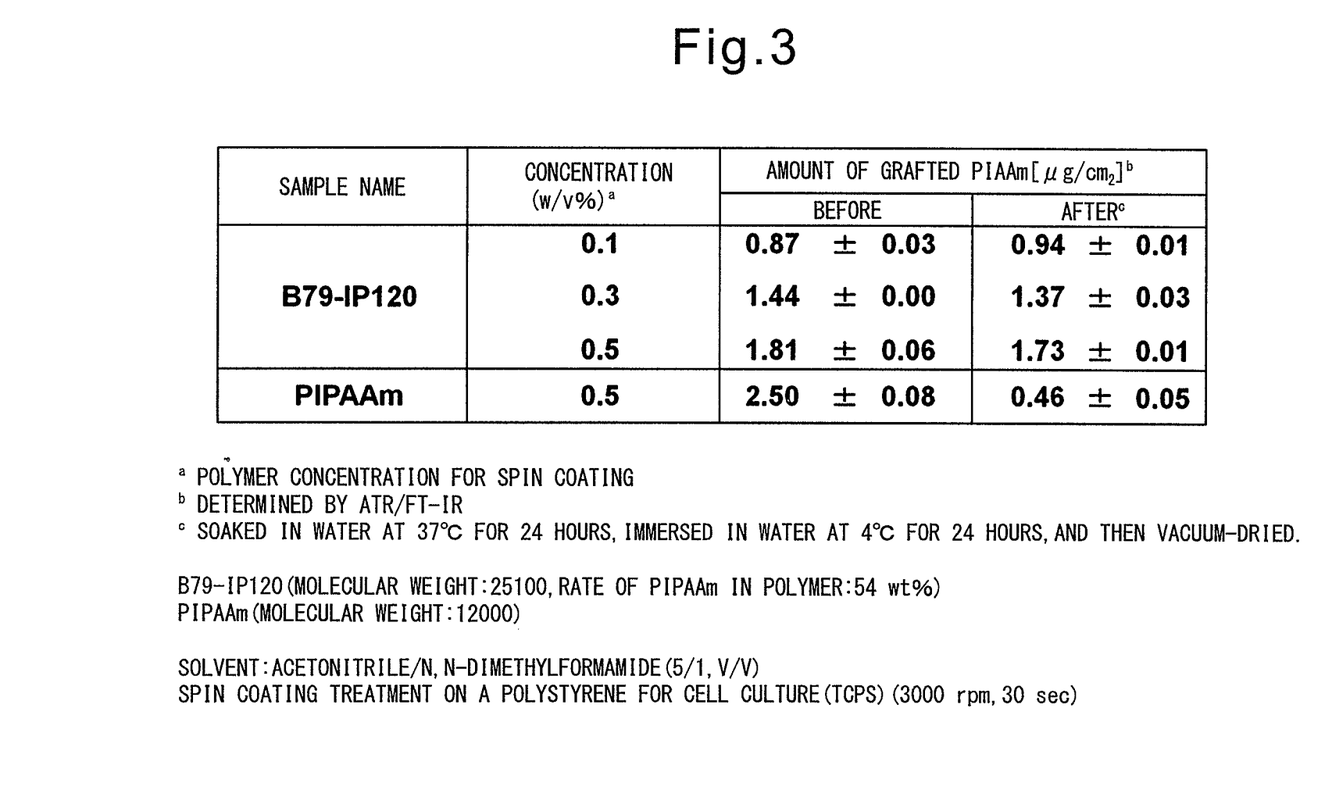
FIG. 3 shows the characteristics of temperature-responsive surfaces obtained in Example 1. The amounts of grafted temperature-responsive polymers and the stability of coating films were evaluated by ATR/FT-IR measurement.
Figure 4:
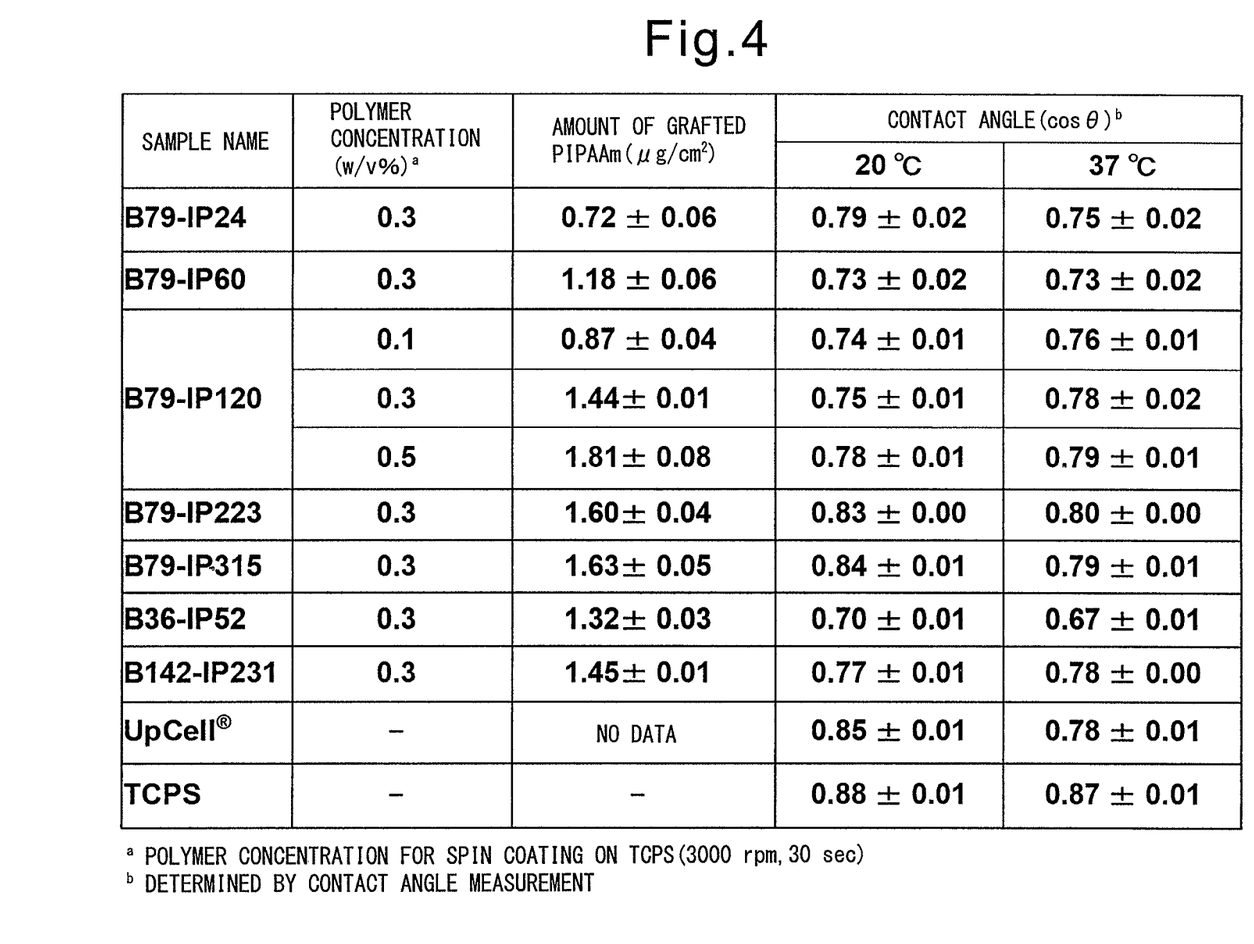
FIG. 4 shows the characteristics of the temperature-responsive surfaces obtained in Example 1. The amounts of immobilized PIPAAm were measured, and surface wettability was also evaluated by static contact angle measurement (underwater bubbling method).

To investigate the stability of polymer coatings in water, the substrates were left standing in water at 37° C. for 24 hours, then shaken in water at 4° C. for 6 hours, and dried under reduced pressure. Firstly, the amount of the polymers on the surface of the base material was determined by an attenuated total reflection Fourier transform infrared spectroscopy (ATR/FT-IR) method to investigate a difference between polymer amounts before the treatment and those after the treatments (see FIG. 3). Then, wettability at 20° C. and 37° C. was evaluated by a static contact angle measurement with an underwater-bubbling method. As a result of investigation of the surface stability of the PBMA-b-PIPAAm-coated substrates using ATR/FT-IR, difference in the amount of grafted PIPAAm was not observed between the substrates before the treatment and those after the treatment (leaving the substrates standing in water at 37° C. for 24 hours and then shaking them in water at 4° C. for 6 hours). This result indicates that the block copolymers remained stably coated on the base materials of the substrates in water during temperature change across LCST (32° C. in the case of PIPAAm) (FIG. 3). It is likely that this result was caused by stable physical adsorption of PBMA, which is a water-insoluble polymer chain, to the polystyrene used as the base material of cell culture substrates, through a hydrophobic interaction. When surface wettability at a temperature over LCST of PIPAAm chain and the wettability at a temperature below the LCST were measured for the polymer-coated substrates, the difference between, them was not observed in the PBMA-b-PIPAAm-coated substrates, as with the PBMA-coated substrates (FIG. 4). Remarkable change was not observed in surface wettability measurement of the PBMA-b-PIPAAm-coated substrates which tracks a macro environmental variation in the PBMA-b-PIPAAm-coated substrates. It is likely that this is because a PBMA chain and a PIPAAm chain are phase-separated to form respective domains on the surface layer of the substrates, unlike the substrate whose surface is wholly covered with PIPAAm which is a temperature-responsive chain, such as a common temperature-responsive cell culture substrate. In addition, it is likely that a phase separation structure can be formed depending on the ratio of a PIPAAm chain to a block copolymer which consists of a PBMA chain and the PIPAAm chain (see FIG. 2).

Example 2

Investigation of Grafted Amount and Cell Behavior

Figure 5:
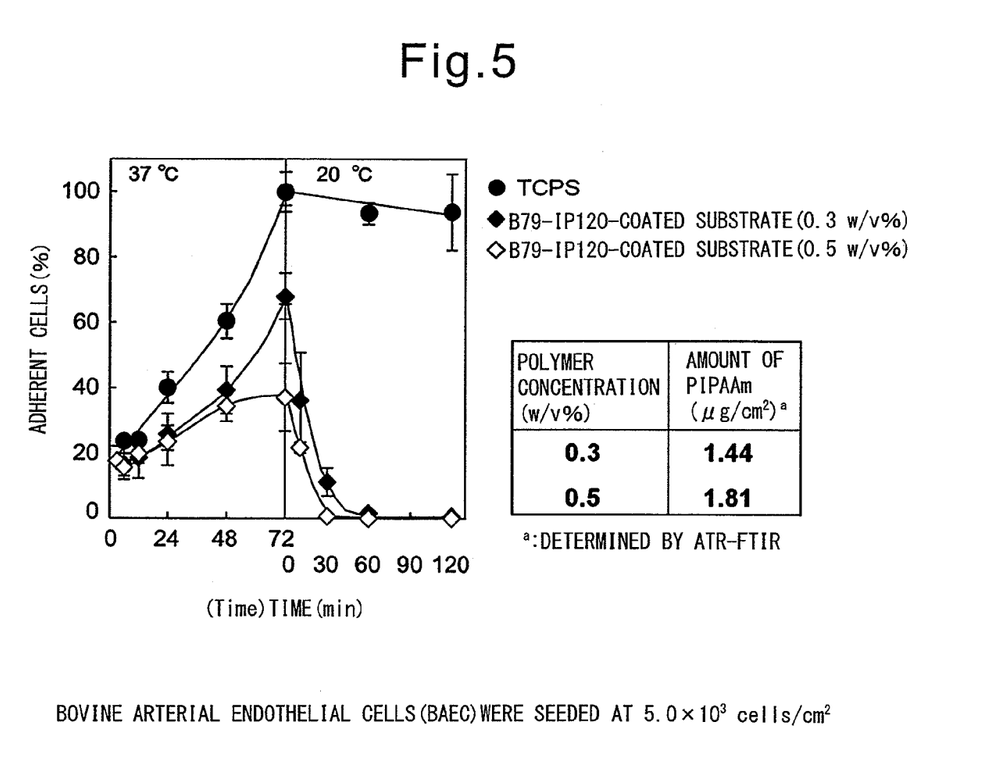
FIG. 5 shows a relationship between cell behavior and a temperature-responsive surface obtained in Example 1 at each grafted amount of the block copolymer.

According to the description of Example 1, substrates in which TCPS was coated with B79-IP120 at various concentrations were prepared. Bovine carotid artery-derived vascular endothelial cells (BAEC) were seeded on the substrates at a concentration of $1.0 \times 10^4$ cells/cm$^2$, and evaluated the adhesiveness of the cells to polymer-coated substrate surfaces at 37° C., and the desorption behaviors of the cells treated with low-temperature of 20° C. A black circle in FIG. 5 indicates a TCPS substrate without coating polymer. Black and white rhombuses in the figure represent changes of cell behavior on substrates in which TCPS was coated with B79-IP120 at 0.3 and 0.5 w/v %, respectively. FIG. 5 indicates changes of cell adhesion rate (%) in the case of seeding BAEC cells on each substrate and then changing culture temperature from 37° C. to 20° C. after 72-hour culture. More specifically, the cell adhesion rates increased during the cell culture at 37° C. The adhesion rate was highest in TCPS for cell culture, and secondly it was higher in the substrate coated with B79-IP120 at 0.3 w/v %. On the other hand, the cell adhesion rate was lowest in the substrate coated with B79-IP120 at 0.5 w/v %. When the amount of PIPAAm coated on TCPS was measured, it was 1.44 µg/cm$^2$ at a concentration of 0.3 w/v %, and 1.81 µg/cm$^2$ at 0.5 w/v %. These results indicate that the greater amount of coated PIPAAm tends to result in a lower cell adhesion rate. In the case of using the substrate coated with PIPAAm whose amount was 1.44 µg/cm$^2$, the cell adhesion rate was remarkably varied when the temperature was changed from 37° C. to 20° C. In the case of using TCPS, change in cell adhesion rate during the temperature change was not almost observed. On the other hand, in the case of using the substrate coated with PIPAAm whose amount was 1.81 µg/cm$^2$, immediate detachment of cells was observed when the temperature was changed from 37° C. to 20° C. However, the cell adhesion rate at 37° C. was low, and thus it would not be preferable for culturing cells.

Figure 6:
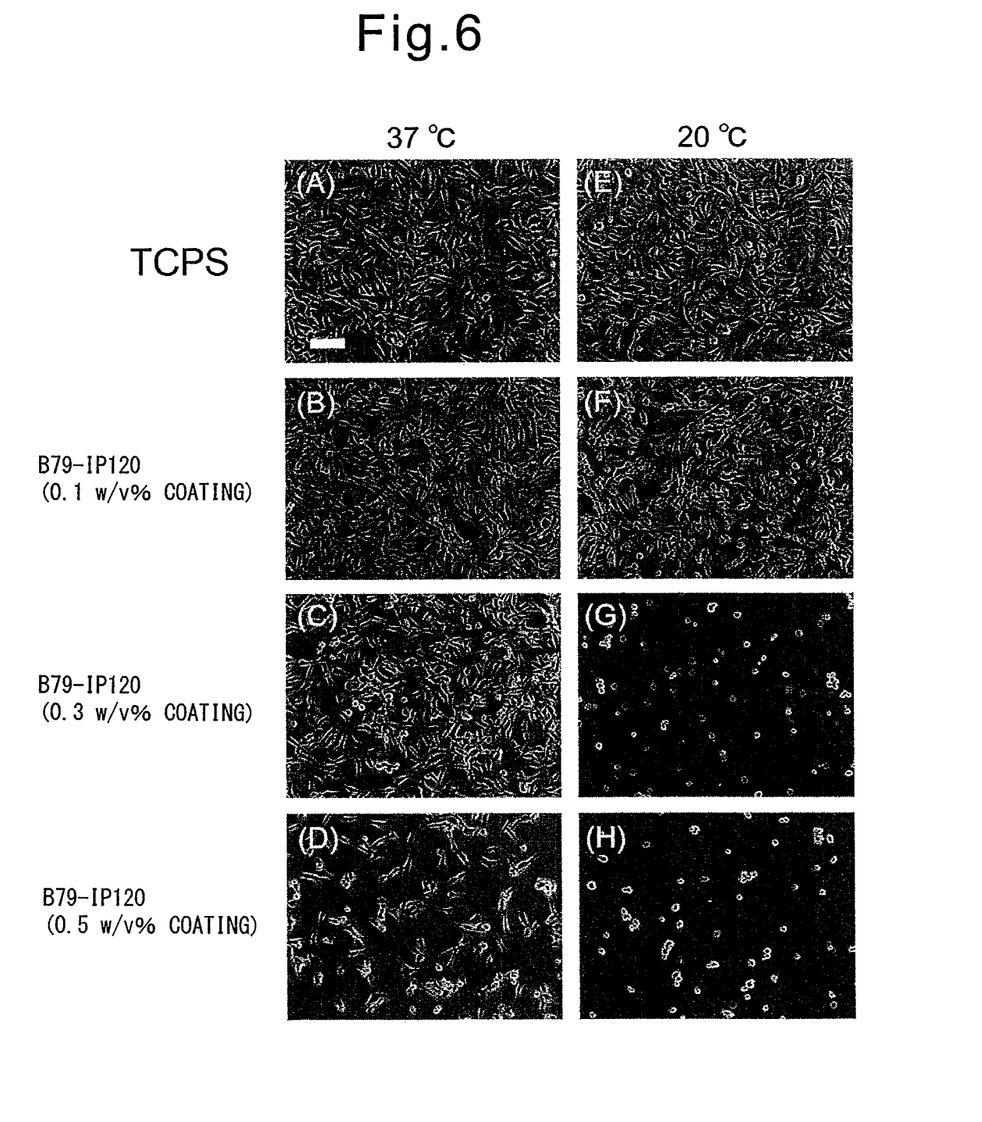
FIG. 6 shows photographs representing a relationship between cell behavior and a temperature-responsive surface obtained in Example 1 at each grafted amount of the block copolymer. Represented are the microphotographs of adherent cells at 72 hours after seeding the cells at 37° C. on TCPS (A), and on the temperature-responsive surfaces which were prepared by coating the TCPS with 0.1 w/v % (B), 0.3 w/v % (C), and 0.5 w/v % (D) of B79-IP120. The morphologies of the cells after decreasing the temperature to 20° C., then culturing for additional 2 hours, are represented in (E) to (H), respectively. The seeding of the cells: 5.0×10$^3$ cells/cm$^2$.

Further, desorption of the BAEC cells, which were cultured on the various substrates described above, during changing temperature was observed, and the results are shown in the photographs. After 3-day culture at 37° C. on the substrate coated with 0.3 w/v % of B79-IP120, cell adhesion and spreading were observed (FIG. 6). Next, a substrate to which cells adhered was treated with low temperature of 20° C. for 2 hours. As a result, it was found that the cells were desorbed voluntarily from the substrate surface. When the same operation was carried out in the PBMA-coated substrates, cell adhesion and spreading were observed, while desorption of cells by the low-temperature treatment was not observed (data not shown). Based on the above results, it is likely that the characteristics of the substrate surface changed to voluntarily detach the adherent cells, since the PIPAAm chain introduced into the substrate surface was hydrated by the low-temperature treatment of LCST or less.

Example 3

Figure 7:
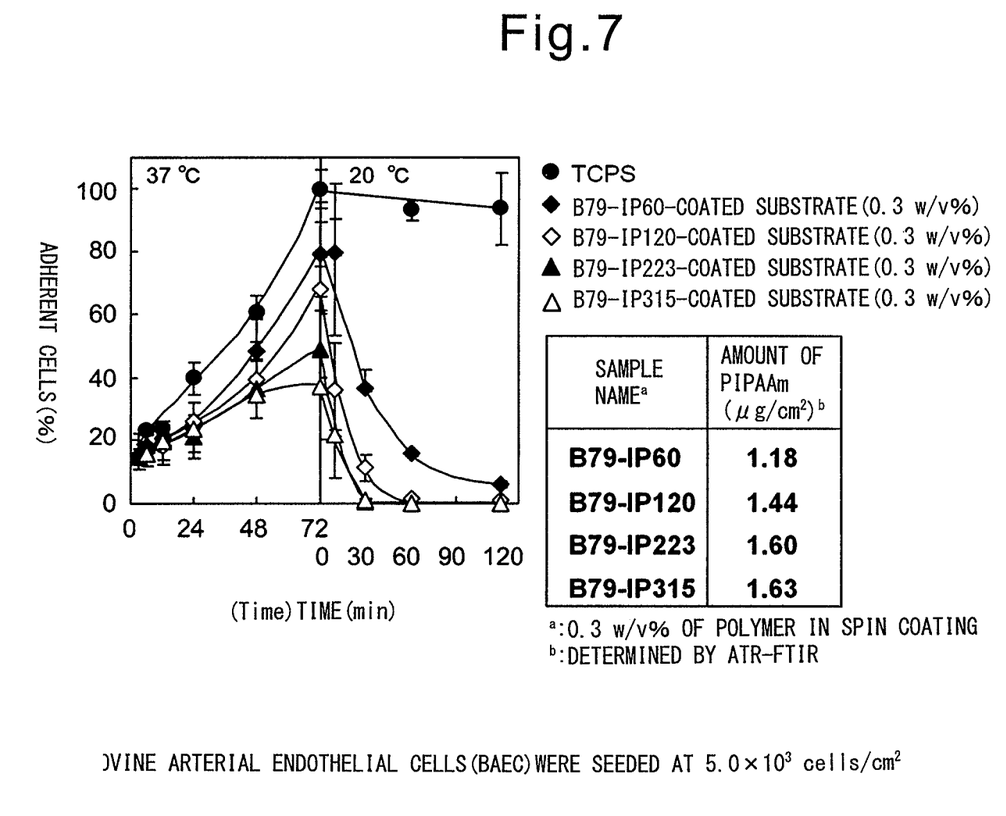
FIG. 7 shows relationships between the molecular chain lengths of PIPAAm and cell behavior.

Detailed Analysis of Change of Cell Behavior Depending on Block Copolymers (1) Relationship Between PIPAAm Molecular Chain Length and Cell Behavior Block copolymers having the constant number of monomer units (the number of monomers) of BMA and varied number of monomer units of IPAAm were prepared according to the production process in Example 1. TCPSs were coated with the block copolymers as described in Example 1, to examine change of the adhesion rate of BAEC cells during changing temperature (FIG. 7). A cell adhesion rate was increased according to decrease of the coated amount of PIPAAm, as with the case of Examples 2. As for cell desorption depending on temperature change, it was found that slow desorption occurred in the substrate coated with PIPAAm whose amount is low (1.18 µg/cm$^2$), compared with the substrates coated with higher amounts (1.44, 1.60, and 1.63 µg/cm$^2$), and that prompt desorption occurred after the temperature change on the substrates coated with high amounts (1.44, 1.60, 1.63 µg/cm$^2$, etc.).

(2) Relationship between Block Copolymer Chain Length and Cell Behavior

Figure 8:
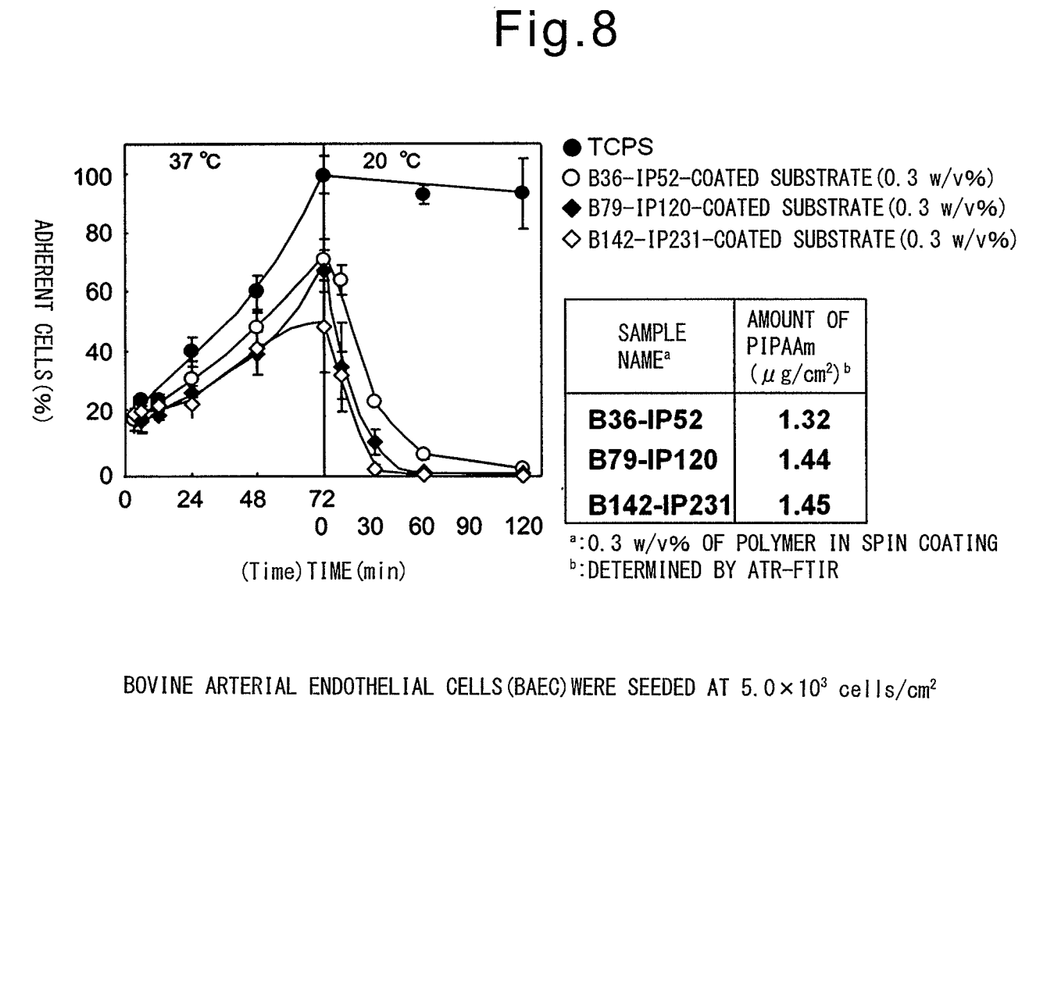
FIG. 8 shows relationships between the chain lengths of block copolymers and cell behavior.

Three kinds of block copolymers having different chain lengths (B36-IP52, B79-IP120, and B142-IP231) were prepared. Substrates which were TCPSs coated with these block copolymers were prepared in the same manner as described in Example 2. Adhesion of BAEC cells seeded on each substrate and change of cell desorption behavior during changing the temperature were evaluated from a cell adhesion rate (FIG. 8). The chain lengths of the three block copolymers were considerably different, but the amounts of PIPAAm in these copolymers coated on TCPS were almost the same, respectively. Remarkable differences in adhesion and desorption properties of the cells seeded on each substrate depending on the chain lengths of the block copolymers were not observed. This result indicates that the amount of PIPAAm grafted on a substrate surface is one of important factors for controlling the adhesion and desorption of cells by temperature change.

(3) Formation of Cell Sheets Using Block Copolymers

Figure 9:
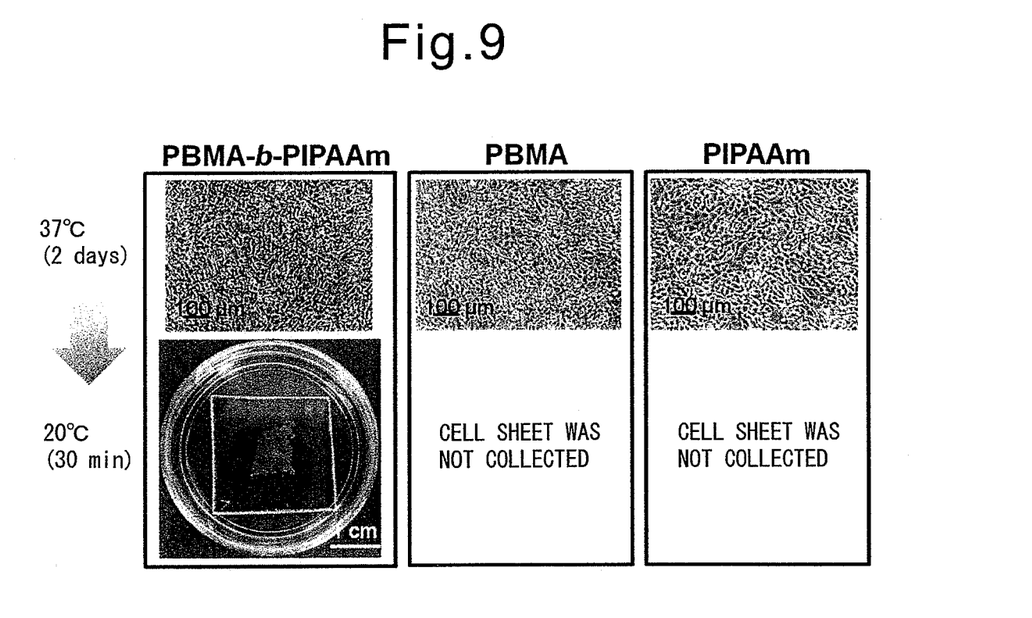
FIG. 9 shows results of cell culture on the temperature-responsive surfaces obtained in Example 1.

FIG. 9 represents the photographs of a cell sheet formed on the substrate coated with the PBMA-b-PIPAAm block copolymer (0.3 w/v % of B79-IP120) and the cell sheet detached by changing a temperature. BAEC cells were cultured at 37° C. on the substrate coated with the PBMA-b-PIPAAm block copolymer (0.3 w/v % of B79-IP120) until being confluent, and then incubated at 20° C. to form the cell sheet which maintains intercellular junctions between adjacent cells.

Figure 10:
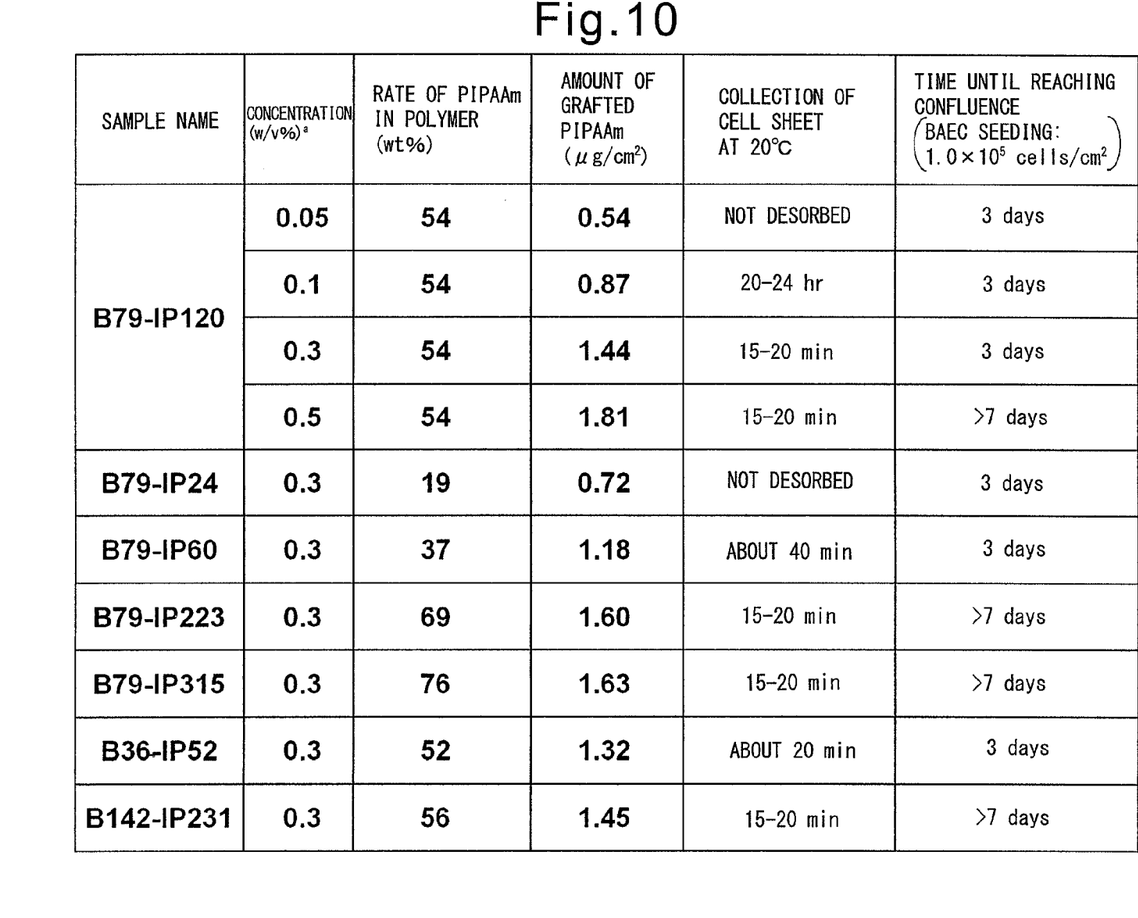
FIG. 10 shows relationships between the temperature-responsive surfaces obtained in Examples 1 to 3 and formation of cell sheets.

Various block copolymers having different chain lengths, monomer units, and grafted amount were prepared. FIG. 10 represents a time required for cells to become confluent on the substrate coated with each block copolymer (period for confluent), and a time from the point of changing temperature at 20° C. to the point of detaching a cell sheet (cell sheet harvest at 20° C.). As a result, it was found that when the amount of coated PIPAAm was high (e.g., 1.45 µg/cm$^2$ or more), the period until the cells become confluent was 7 days or more. On the other hand, it was found that when the amount of coated PIPAAm was less than 0.8 µg/cm$^2$, cells could not be detached and cell sheet was not formed. Based on the above results, cell culture and the detachment of cultured cells or a cell sheet by changing temperature will be efficiently performed by using a substrate surface coated with PBMA-b-PIPAAm.

Comparative Example 1

Preparation of Temperature-Responsive Surface Using Aqueous Solvent

B79-IP120 used in Example 2 was attempted to be dispersed in water at a concentration of 0.1 w/v %. As a result, this polymer was not dispersed or emulsified in water, and any homogeneous solution was not obtained. A TCPS substrate surface was coated with the obtained solution, but the substrate surface became heterogeneous to an extent visually observed. Therefore, it was not preferable for the present invention.

INDUSTRIAL APPLICABILITY

Cells obtained from each tissue can be efficiently cultured by using the temperature-responsive cell culture substrate of the present invention. This culturing method makes it possible to detach cultured cells or a cell sheet efficiently without damage only by changing temperature.

The invention claimed is:

1. A temperature-responsive substrate for cell culture, wherein a base material surface of the substrate is coated with a block copolymer, in which a water insoluble polymer segment is coupled with a temperature-responsive polymer segment, in an amount of 0.8 to 3.0 µg/cm$^2$ of the temperature-responsive polymer, wherein a content of the temperature-responsive polymer in the block copolymer is 30 to 90 wt %.

2. The temperature-responsive substrate for cell culture according to claim 1, wherein the base material surface of the substrate is coated with the block copolymer in an amount of 0.09 to 7.0 µg/cm$^2$ of the water insoluble polymer.

3. The temperature-responsive substrate for cell culture according to claim 1, wherein the substrate surface has a phase separation structure.

4. The temperature-responsive substrate for cell culture according to claim 1, wherein an average molecular weight of the temperature-responsive polymer in the block copolymer is 3000 or more.

5. The temperature-responsive substrate for cell culture according to claim 1, wherein the temperature-responsive polymer comprises any one or more of poly-N-substituted acrylamide derivatives, poly-N-substituted methacrylamide derivatives, their copolymers, and polyvinyl methyl ethers.

6. The temperature-responsive substrate for cell culture according to claim 1, wherein the temperature-responsive polymer is poly-N-isopropylacrylamide.

7. The temperature-responsive substrate according to claim 1, wherein a base material of the substrate is one plate-shaped base material or a combination of two or more plate-shaped base materials.

8. A method for producing a temperature-responsive substrate for cell culture, wherein a base material surface of the substrate is coated with a block copolymer, in which a water insoluble polymer segment is coupled with a temperature-responsive polymer segment, in an amount of 0.8 to 3.0 µg/cm$^2$ of the temperature-responsive polymer, wherein a content of the temperature-responsive polymer in the block copolymer is 30 to 90 wt %, the method comprising the following steps of:
dissolving or dispersing in an organic solvent the block copolymer in which the water insoluble polymer segment is coupled with the temperature-responsive polymer segment;
applying the block copolymer solution homogeneously to a base material surface by spin coating; and drying the surface.

9. The method for producing the temperature-responsive substrate for cell culture according to claim 8, wherein the block copolymer is obtained by reversible addition-fragmentation chain transfer (RAFT) polymerization.

10. The method for producing the temperature-responsive substrate for cell culture according to claim 8 or 9, wherein the solvent in which the block copolymer is dissolved is a liquid mixture of acetonitrile and N,N-dimethylformamide.

11. The method for producing the temperature-responsive substrate for cell culture according to claim 10, wherein a volume ratio of acetonitrile to N,N-dimethylformamide in the liquid mixture is 5:1.

* * * * *